US011123202B2

(12) United States Patent
Kurtaliaj et al.

(10) Patent No.: US 11,123,202 B2
(45) Date of Patent: Sep. 21, 2021

(54) SPINAL IMPLANTS AND INSTRUMENTS

(71) Applicant: GLOBUS MEDICAL, INC., Audubon, PA (US)

(72) Inventors: Iden Kurtaliaj, Philadelphia, PA (US); Kevin Gahman, Douglassville, PA (US); Chad Glerum, Pennsburg, PA (US); John Matthews, Philadelphia, PA (US); Douglas Cahill, Lititz, PA (US); Ross Morris, Carlisle, PA (US); Scott Myers, Lansdale, PA (US); Michael Zweizig, Fleetwood, PA (US); Patrick J. Nolan, Cinnaminson, NJ (US); Patrick Murray, Collegeville, PA (US); Victoria Michna, Wayne, NJ (US); Aditya Muzumdar, King of Prussia, PA (US); Aditya Ingalhalikar, King of Prussia, PA (US)

(73) Assignee: Globus Medical Inc., Audubon, PA (US)

( * ) Notice: Subject to any disclaimer, the term of this patent is extended or adjusted under 35 U.S.C. 154(b) by 214 days.

(21) Appl. No.: 15/905,974

(22) Filed: Feb. 27, 2018

(65) Prior Publication Data
US 2018/0185169 A1    Jul. 5, 2018

Related U.S. Application Data

(63) Continuation of application No. 14/538,136, filed on Nov. 11, 2014, now Pat. No. 9,931,226.

(51) Int. Cl.
*A61F 2/46* (2006.01)
*A61B 17/70* (2006.01)
(Continued)

(52) U.S. Cl.
CPC ........ *A61F 2/4611* (2013.01); *A61B 17/7074* (2013.01); *A61B 17/7076* (2013.01);
(Continued)

(58) Field of Classification Search
CPC .............. A61B 17/708; A61B 17/7074; A61B 17/8863; A61B 17/8861; A61B 17/8894;
(Continued)

(56) References Cited

U.S. PATENT DOCUMENTS

| | | | |
|---|---|---|---|
| 2012/0089150 A1* | 4/2012 | Smith ................ | A61B 17/7076 606/104 |
| 2012/0109208 A1* | 5/2012 | Justis ................. | A61B 17/7089 606/264 |
| 2014/0180298 A1* | 6/2014 | Stevenson ............ | A61B 17/708 606/104 |

* cited by examiner

*Primary Examiner* — Amy R Sipp

(57) ABSTRACT

An intervertebral spacer inserter includes a sleeve having a longitudinal axis, a hollow sleeve bore extending through the sleeve along the longitudinal axis, a sleeve tip end and an opening of a passage disposed in the sleeve tip end. The passage extends into the sleeve to the sleeve shaft along a passage axis that intersects the longitudinal axis at an angle less than about 90°. A sliding tip with an elongated slot is in contact with the sleeve tip end and is moveable with respect to the sleeve tip end between a first position with the opening accessible through the elongated slot and disposed adjacent a first end of the elongated slot and a second position with the opening accessible through the elongated slot and disposed adjacent a second end of the elongated slot opposite the first end.

10 Claims, 12 Drawing Sheets

(51) Int. Cl.
*A61B 17/88* (2006.01)
*A61F 2/30* (2006.01)
(52) U.S. Cl.
CPC .......... *A61B 17/7086* (2013.01); *A61B 17/88* (2013.01); *A61B 17/8863* (2013.01); *A61B 17/7032* (2013.01); *A61F 2002/30387* (2013.01); *A61F 2002/30505* (2013.01); *A61F 2002/30708* (2013.01); *A61F 2002/4622* (2013.01); *A61F 2002/4627* (2013.01); *A61F 2002/4628* (2013.01); *A61F 2002/4629* (2013.01)
(58) Field of Classification Search
CPC ...... A61B 17/7076; A61F 2/4611; A61F 2/46; A61F 2002/4622; A61F 2002/4625; A61F 2002/4627; A61F 2002/4628
See application file for complete search history.

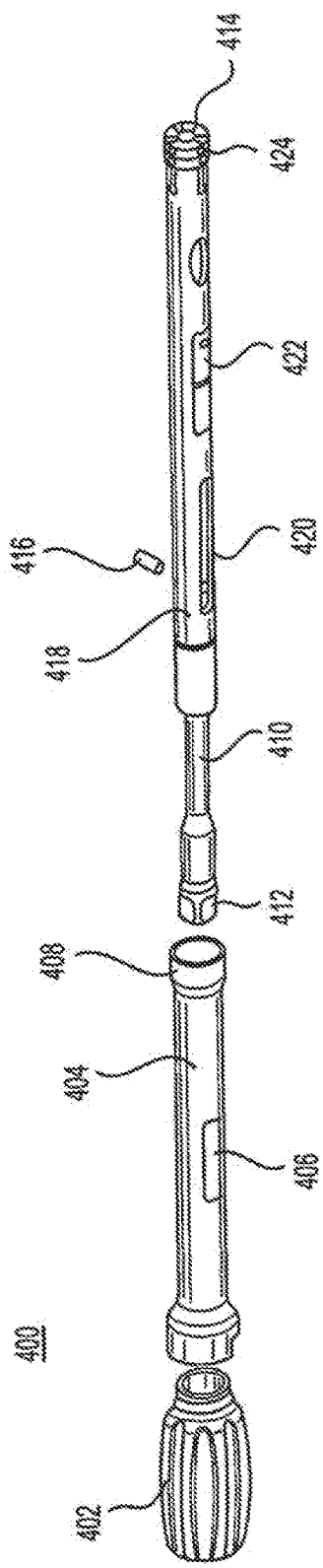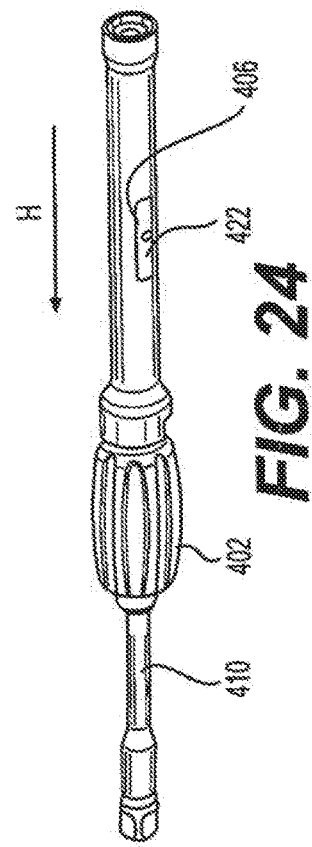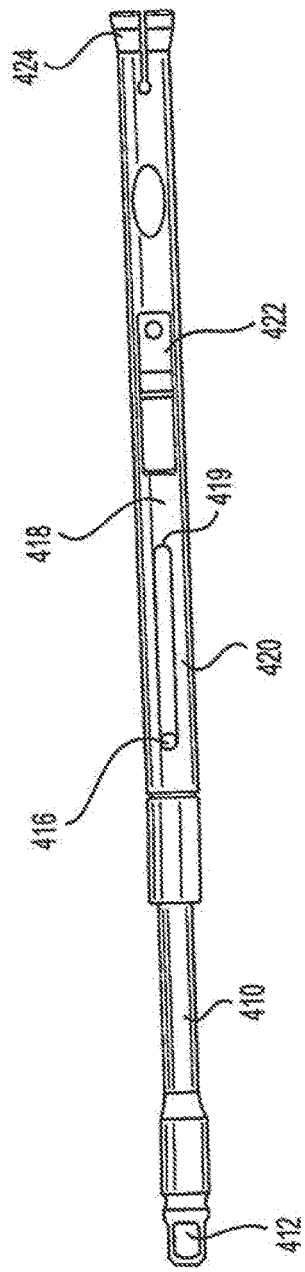

SPINAL IMPLANTS AND INSTRUMENTS

CROSS REFERENCE TO RELATED APPLICATIONS

This application is a continuation of U.S. patent application Ser. No. 14/538,136, titled "Spinal Implants and Instruments," filed on Nov. 11, 2014, the entire disclosure of which is incorporated by reference herein in its entirety.

FIELD OF THE INVENTION

The present invention relates to implants and instruments for use in spinal surgery.

BACKGROUND OF THE INVENTION

Repair and stabilization of the thoracolumbar region of the spine for coronal plane and sagittal plane reduction and intervertebral spacer insertion utilizes various tools and implants. These tools provide access to the thoracolumbar region, insertion of spacers, insertion of pedicle screws and other anchors and attachment of rods to these screws and anchors. Improved tools for anchor insertion, rod reduction, reduction screw tab removal and spacer insertion are desired.

For example, various techniques are currently being used to fuse lumbar spine vertebrae to treat specific types of spine disorders and to alleviate pain. These include the minimally invasive procedure lateral lumbar interbody fusion (LLIF) that accesses the intervertebral disc space and fuses the lumbar spine using a side (lateral) surgical approach rather than a front (anterior) or back (posterior) approach. As a minimally invasive approach, LLIF reaches the spine through several small incisions, reducing tissue trauma, scarring, post-operative discomfort and pain medication use.

The LLIF approach facilitates a 90° vertical reach parallel to the disc and the posterior wall of the vertebrae. Specifically in patients with coronal deformity, discs are often approached from the concave side, which permits easier access and reduces the number of incisions. However, access to L4-L5 makes an exception due to the position of the iliac crest. In patients with a coronally oblique L4-L5 disc and a high crest, a convex side approach is used. If the mid lumbar concave approach and the side of the L4-L5 approach do not correspond, a contralateral L4-L5 approach is used. After posterior fixation, table break cannot be used to open the space between the ribs and the iliac crest. Therefore, L4-L5 cannot be reached without angled measurements.

In addition to the limited number of disc levels that can be accessed, patient specific anatomy can provide for only a left or right approach. Before surgery, the width of the working window to each space is checked by looking at the position of the vessels and lobar plexus in axial MRI/CT slices. Depending on the axial anatomy, one side could be considered safer for access than the over side.

Angled inserters that are connected to intervertebral spaces having a centered attachment point allow for the instrument to be used for both a left approach and a right approach. However, if the attachment point of the intervertebral spacer is off center, then two separate inserter instruments are required based on the direction of approach. These separate inserters have a fixed alignment and spacer attachment based on the direction of approach. Therefore, a single angled inserter instrument is desired that can be used for both left and right approaches during an LLIF procedure.

SUMMARY OF THE INVENTION

Exemplary embodiments in accordance with the present invention are directed to methods and systems for using an angled intervertebral spacer inserter during a LLIF procedure in the thoracolumbar region of the spine and in particular in the L4-L5 disc level. The instrument assists in access to the desired disc level during an LLIF procedure and is used to reach the upper levels of the lumbar spine where, depending on patient specific anatomy, ribs may interfere with a 90° vertical approach during the LLIF procedure. Suitable embodiments connect to an intervertebral spacer having an off centered point of connection for purposes of either a left of right approach.

In one embodiment, an intervertebral spacer inserter is provided having a sleeve with a longitudinal axis, a hollow sleeve bore extending through the sleeve along the longitudinal axis and a sleeve tip end. An opening of a passage is disposed in the sleeve tip end, and the passage extends into the sleeve to the sleeve shaft along a passage axis that intersects the longitudinal axis at an angle less than about 90°. In one embodiment, the angle is about 15°. Alternatively, the angle is adjustable up to about 90°. A slap handle is attached to the sleeve at a handle end opposite the sleeve tip end. In one embodiment, the sleeve tip end includes a flat surface. This flat surface is disposed in a plane perpendicular to the passage axis, and the opening disposed in the flat surface.

The intervertebral spacer inserter includes a sliding tip having an elongated slot. The sliding tip is in contact with the sleeve tip end and is moveable with respect to the sleeve tip end between a first position with the opening accessible through the elongated slot and disposed adjacent a first end of the elongated slot and a second position with the opening accessible through the elongated slot and disposed adjacent a second end of the elongated slot opposite the first end. In one embodiment, the sliding tip has a first face in contact with the sleeve tip end, e.g., the flat surface, and a second face opposite the first face. The elongated slot passes completely through the sliding tip from the first face to the second face. In one embodiment, the first face is shaped as a channel having a bottom surface, and the sleeve tip end extends into the channel such that the flat surface is in contact with the bottom surface of the channel. Suitable shapes for the channel include a dove tail shaped cross section.

The elongated slot has a midpoint between the first end and the second end. The opening is accessible through the elongated slot between the midpoint and the first end when the sliding tip is in the first position, and the opening is accessible through the elongated slot between the midpoint and the second end when the sliding tip is in the second position. In one embodiment, the sliding tip has a first edge and a second edge disposed opposite the first edge and defining a length between the first and second edges. The elongated slot is aligned parallel to the length. In addition, the sliding tip has a pair of tangs extending from the sliding tip away from the sleeve tip end. One tang is disposed at each of the first edge and the second edge of the sliding tip.

The intervertebral spacer inserter also includes a first alignment mechanism disposed between the flat surface and the first face to hold the sliding tip in the first position and a second alignment mechanism separate from the first alignment mechanism and disposed between the flat surface and the first face. The alignment mechanism holds the sliding tip in the second position. In one embodiment, the first alignment mechanism includes a first recess disposed in the first face, a first cavity disposed in the flat surface and a first spring loaded ball plunger disposed in the first cavity and biased outward from the first cavity toward the first face. The first spring loaded ball plunger engages the first recess when the sliding tip is in the first position. Similarly, the second alignment mechanism includes a second recess disposed in the first face, a second cavity disposed in the flat surface and a second spring loaded ball plunger disposed in the second cavity and biased outward from the second cavity toward the first face. The second spring loaded ball plunger engages the second recess when the sliding tip is in the second position.

The intervertebral spacer inserter includes a drive shaft rotatably disposed in the hollow sleeve bore. This drive shaft has a distal end disposed adjacent the sleeve tip end. A connection tip is rotatably disposed in the passage and is in contact with the distal end of the drive shaft. This connection tip has a threaded end that extends through the opening and the elongated slot. In one embodiment, the distal end of the drive shaft is shaped as a ball, and the connection tip further is provided with a socket end opposite the threaded end such that the ball engaged in the socket end. The drive shaft also includes an enlarged knobbed wheel disposed adjacent a proximal end opposite the distal end. This enlarge knobbed wheel is accessible through the sleeve.

The present invention is also directed to an intervertebral spacer inserter having a sleeve with a sleeve tip end and a connection tip extending out from the sleeve tip end. A sliding tip with an elongated slot is included, and the connection tip extends through the elongated slot. This sliding tip is in contact with the sleeve tip end and is moveable with respect to the sleeve tip end between a first position with the connection tip disposed adjacent a first end of the elongated slot and a second position with connection tip disposed adjacent a second end of the elongated slot opposite the first end. In one embodiment, the elongated slot has a midpoint between the first end and the second end. The connection tip is disposed between the midpoint and the first end when the sliding tip is in the first position, and the connection tip is disposed between the midpoint and the second end when the sliding tip is in the second position.

In one embodiment, the sliding tip further has a first face in contact with the sleeve tip end and a second face opposite the first face. The elongated slot passes completely through the sliding tip from the first face to the second face. When the sleeve tip end includes a flat surface, the first face is in contact with the flat surface. The intervertebral spacer inserter is provided with a first alignment mechanism disposed between the flat surface and the first face to hold the sliding tip in the first position; and a second alignment mechanism separate from the first alignment mechanism and disposed between the flat surface and the first face to hold the sliding tip in the second position. In one embodiment, the first alignment mechanism includes a first recess disposed in the first face, a first cavity disposed in the flat surface and a first spring loaded ball plunger disposed in the first cavity and biased outward from the first cavity toward the first face. The first spring loaded ball plunger engages the first recess when the sliding tip is in the first position. Similarly, the second alignment mechanism includes a second recess disposed in the first face, a second cavity disposed in the flat surface and a second spring loaded ball plunger disposed in the second cavity and biased outward from the second cavity toward the first face. The second spring loaded ball plunger engages the second recess when the sliding tip is in the second position.

BRIEF DESCRIPTION OF THE DRAWINGS

FIG. 23 is an exploded perspective view of an embodiment of a retractable rigid screwdriver in accordance with the present invention;
FIG. 24 is a perspective view of the retractable rigid screwdriver;
and
FIG. 25 is a side view of the driver shaft and the retracting shaft of the retractable rigid screw driver.

DETAILED DESCRIPTION

Figure 1:
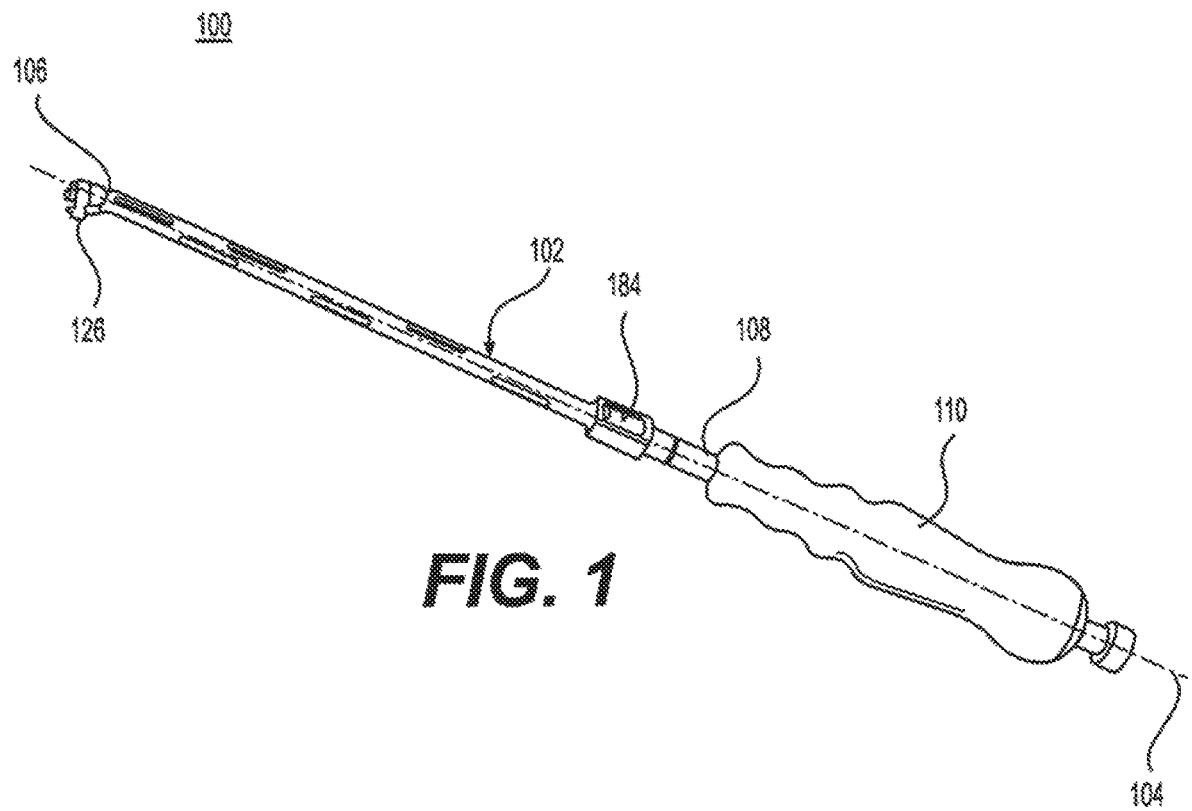
FIG. 1 is a perspective view of an embodiment of an intervertebral spacer inserter in accordance with the present invention.
Figure 2:
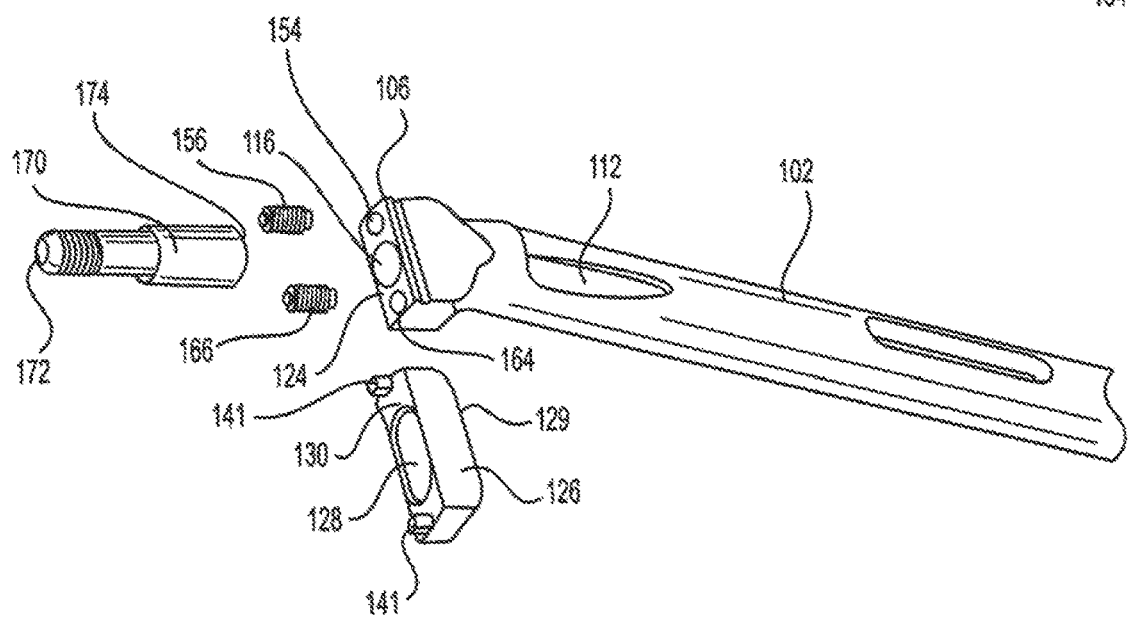
FIG. 2 is a partial exploded view of the intervertebral spacer inserter.
Figure 3:
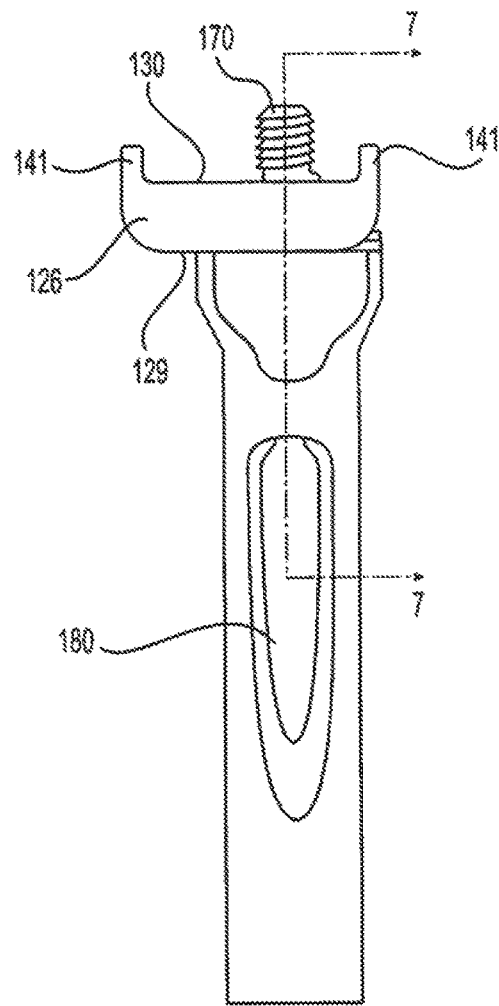
FIG. 3 is a top view of one end of the intervertebral spacer inserter with the sliding tip in the first position.
Figure 4:
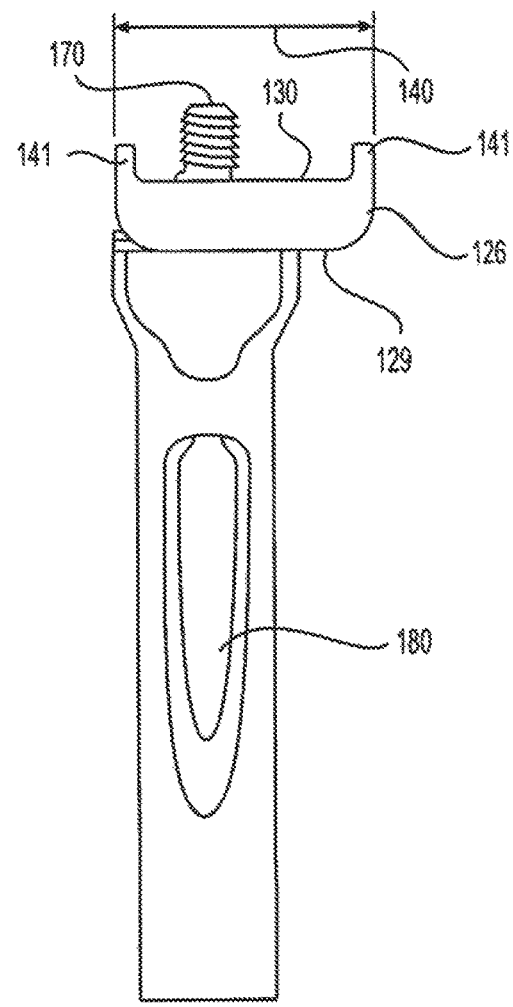
FIG. 4 is a top view of one end of the intervertebral spacer inserter with the sliding tip in the second first position.
Figure 5:
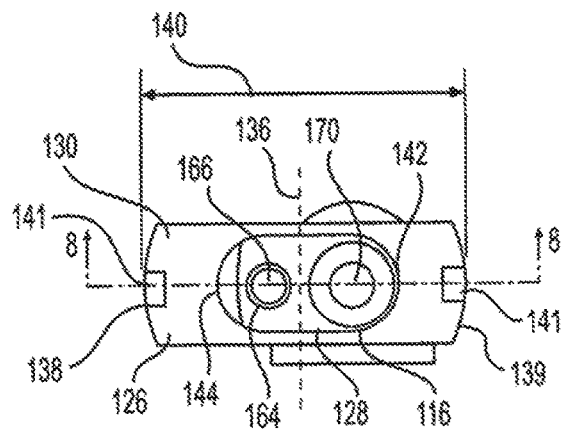
FIG. 5 is an end view of the sleeve tip end of the intervertebral spacer inserter with the sliding tip in the first position.
Figure 6:
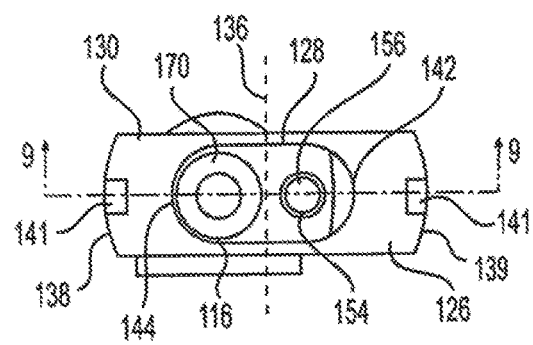
FIG. 6 is an end view of the sleeve tip end of the intervertebral spacer inserter with the sliding tip in the first position.

Referring initially to FIGS. 1-9, an exemplary embodiment of the present invention is directed to an intervertebral spacer inserter 100. The intervertebral spacer inserter facilitates minimally invasive techniques for spacer insertion in the thoracolumbar region of the spine using a side (lateral) surgical approach, such as lateral lumbar interbody fusion (LLIF). The intervertebral spacer inserter can be used for either a left or right side approach with a spacer having an off-center point of connection. This is accomplished with an intervertebral spacer inserter having a curved tip end attached to a sliding tip. As illustrated, the intervertebral spacer inserter 100 includes a sleeve 102 running along a longitudinal axis 104 with a sleeve tip end 106 and a handle end 108 opposite the sleeve tip end 106. A handle, for example, a slap handle, is attached to the sleeve at the handle end. Suitable arrangements of slap handles are known and available in the art.

The sleeve includes a hollow sleeve bore 112 (FIGS. 2 and 7-9) extending through the sleeve along the longitudinal axis from the sleeve tip end to the handle end. In one embodiment, the hollow sleeve bore has a circular cross-section. Disposed in the sleeve tip end 106 is an opening 116 (FIG. 2), for example a circular opening, of a passage 118 (FIG. 7) that extends into the sleeve along a passage axis 120. The passage is in communication with the sleeve shaft 112, and the passage axis 120 intersects the longitudinal axis 104 at an angle 122 less than about 90°. In one embodiment, the angle is about 15°. Alternatively, the angle is adjustable up to about 90°. This angle provides and defines the curved tip end of the intervertebral spacer inserter. In one embodiment, the sleeve tip end has a flat surface 124 (FIG. 2), and the opening is disposed on this flat surface. Preferably, the flat surface is disposed in a plane that extends perpendicular to the passage axis 120.

Figure 7:
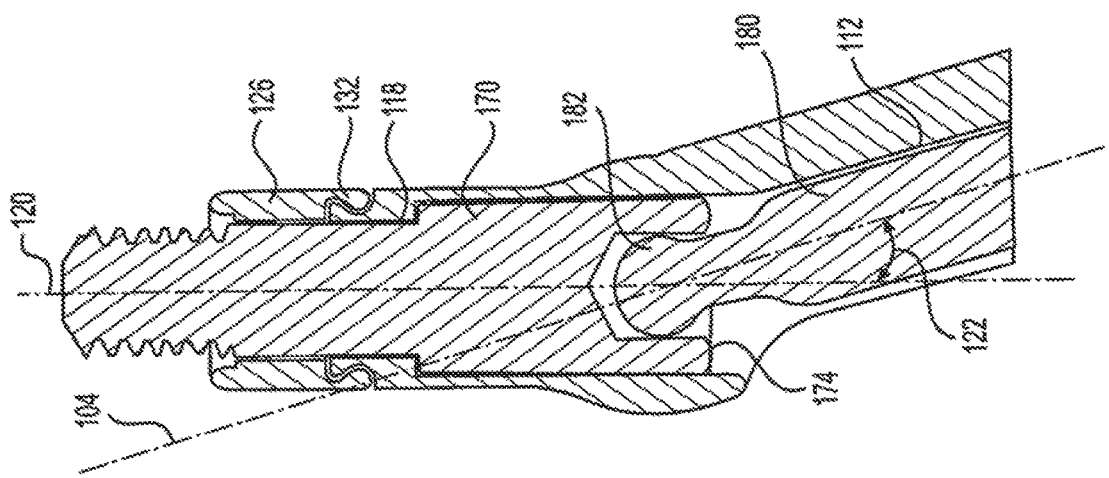
FIG. 7 is a view through line 7-7 of FIG. 3.

The intervertebral spacer inserter 100 also includes a sliding tip 126 that is in contact with the sleeve tip end 106 of the sleeve. Preferably, the sliding tip end is a separate structure than the sleeve (FIG. 2) and can be completely separated and removed from the sleeve. In general, the sliding tip includes a first face 129 that faces or is in contact with the sleeve tip end. In one embodiment, the first face is in contact with the flat surface of the sleeve tip end. The sliding tip also includes a second face 130 opposite the first face 129. The second face 130 contacts or engages any spacer 131 (FIGS. 10-12) that is attached to the intervertebral spacer inserter. The sliding tip includes an elongated slot 128. The elongated slot 128 passes completely through the sliding tip from the first face to the second face. In order to provide secure attachment of the sliding tip to the sleeve tip end, in one embodiment the first face is formed as a channel 132 (FIGS. 8 and 9) having a bottom surface 134. The sleeve tip end extends into the channel, and the flat surface of the sleeve tip end contacts with the bottom surface of the channel. In order to constrain movement of the sliding tip relative to the sleeve tip end along a given line, the channel has a dove tail shaped cross section (FIG. 7). The sleeve tip end is formed in a mating shape to the dove tail shaped channel.

The sliding tip can be any desired or suitable shape. In one embodiment, when viewed from the first or second faces, the sliding tip has a generally rectangular shape. In this embodiment, the sliding tip includes a first edge 138 and a second edge 139 disposed opposite the first edge. This defines a length 140 between the first and second edges. In the rectangular arrangement, this length represents the longer length of the rectangular shape of face of the sliding tip. The channel is aligned with this length, and the elongated slot is also aligned parallel to the length. Movement of the sliding tip relative to the sleeve tip end is also along the direction of this length. The elongated slot includes a first end 142, a second end 144 and a midpoint 136 between the first end and the second end. Preferably, the midpoint of the elongated slot is aligned with the midpoint of the length of the sliding tip. The sliding tip includes a pair of tangs 141 extending from the sliding tip away from the sleeve tip end. One tang is disposed at each of the first edge and the second edge of the sliding tip.

The sliding tip moves with respect to the sleeve tip end between a first position (FIGS. 3, 5 and 8) with the opening accessible through the elongated slot and disposed adjacent a first end of the elongated slot and a second position (FIGS. 4, 6 and 9) with the opening accessible through the elongated slot and disposed adjacent a second end of the elongated slot opposite the first end. Preferably, the opening is accessible through the elongated slot and is between the midpoint and the first end when the sliding tip is in the first position, and the opening is accessible through the elongated slot and is disposed between the midpoint and the second end when the sliding tip is in the second position. Therefore, the sliding tip moves between two non-centered or offset positions with respect to the its midpoint and the opening in the sleeve tip end, facilitating the use of the intervertebral spacer inserter in either a left or right side lateral approach.

In order to secure or hold the sliding tip in either the first or second position, alignment mechanisms are provided between the sleeve tip end and the sliding tip. Suitable alignment mechanisms can include, for sample, an indentation and a moveable member that is biased into the indentation when the sleeve tip end and the sliding tip are in the desired arrangement. A single alignment mechanism can be provided for both the first and second positions, or a separate alignment mechanism can be provided for each one of the first position and the second position. In one embodiment, the alignment mechanism includes a first alignment mechanism disposed between the flat surface and the first face to hold the sliding tip in the first position and a second alignment mechanism separate from the first alignment mechanism and disposed between the flat surface and the first face to hold the sliding tip in the second position.

Figure 9:
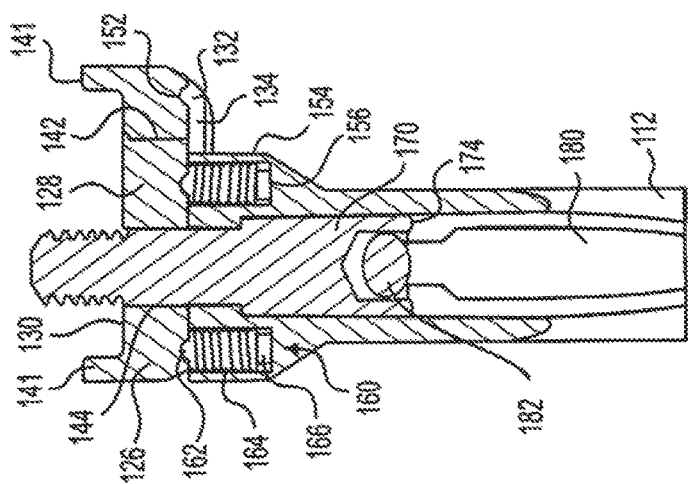
FIG. 9 is a view through line 9-9 of FIG. 6.
Figure 8:
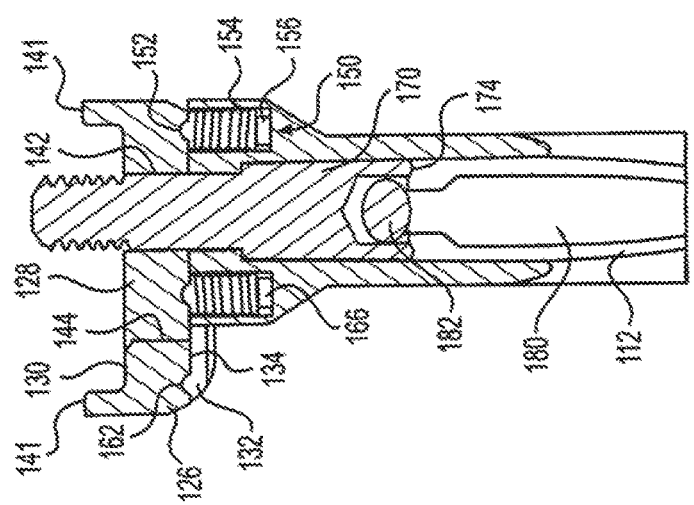
FIG. 8 is a view through line 8-8 of FIG. 5.

As illustrated in the drawings, the first alignment mechanism 150 includes a first recess 152 disposed in the first face, a first cavity 154 disposed in the flat surface and a first spring loaded ball plunger 156 disposed in the first cavity and biased outward from the first cavity toward the first face. The first spring loaded ball plunger engages the first recess when the sliding tip is in the first position (FIG. 8). The second alignment mechanism 160 includes a second recess 162 disposed in the first face, a second cavity 164 disposed in the flat surface and a second spring loaded ball plunger 166 disposed in the second cavity and biased outward from the second cavity toward the first face. The second spring loaded ball plunger engages the second recess when the sliding tip is in the second position (FIG. 9).

The intervertebral spacer inserter includes a drive shaft 180 rotatably disposed in the hollow sleeve bore. The drive shaft includes a distal end 182 disposed adjacent the sleeve tip end. In one embodiment, the drive shaft includes an enlarged grooved or knobbed wheel 184 disposed adjacent a proximal end opposite the distal end and adjacent the attached handle. The enlarged knobbed wheel is accessible through the sleeve (FIG. 1). A connection tip 170 is provided that is rotatably disposed in the passage and is in contact with the distal end of the drive shaft. The connection tip includes a threaded end 172 that extends out from the passage through the opening and the elongated slot. Therefore, the connection tip also prevents the sliding tip from completely sliding off the sleeve tip end. The opposite end of the connection tip is functionally engaged with the distal end of the drive shaft so that rotation of the drive shaft rotates the connection tip. In one embodiment, the distal end of the drive shaft is shaped as a ball 182, and the connection tip includes a socket end 174 opposite the threaded end. The ball is engaged in the socket end to provide a working connection at the desired angle.

Figure 10:
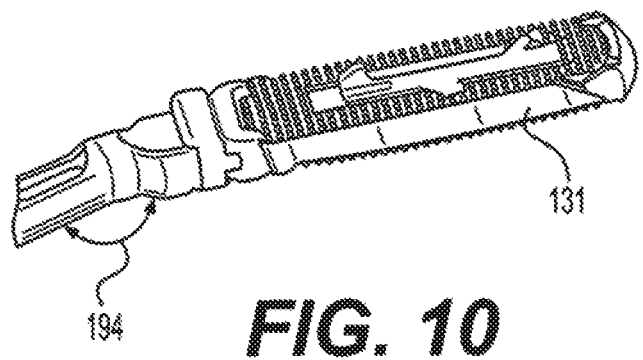
FIG. 10 is a perspective view of an end of the intervertebral spacer inserter with a spacer attached.
Figure 11:
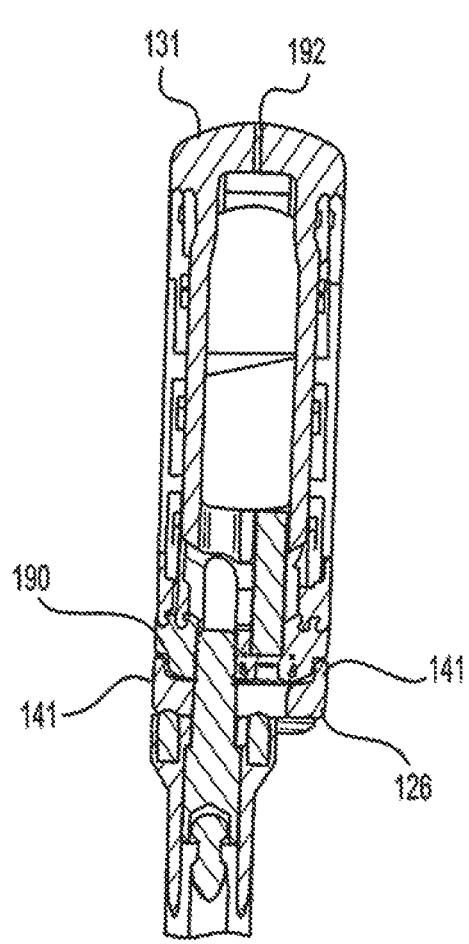
FIG. 11 is the view of FIG. 9 with the spacer attached.
Figure 12:
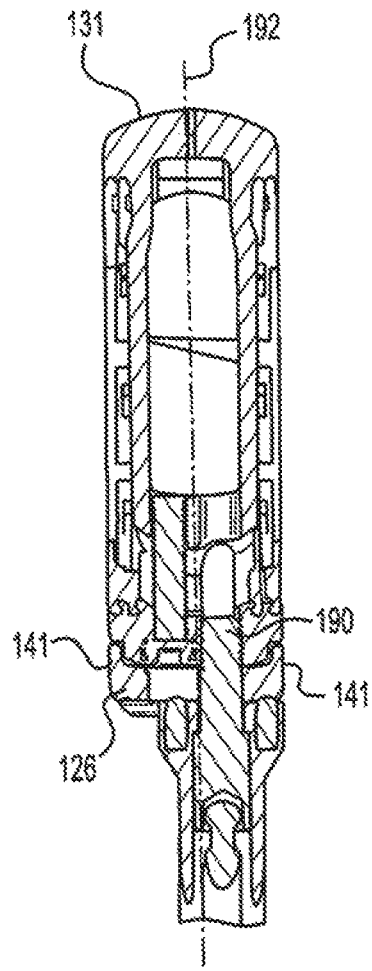
FIG. 12 is the view of FIG. 8 with the spacer attached.
Figures 13, 14:
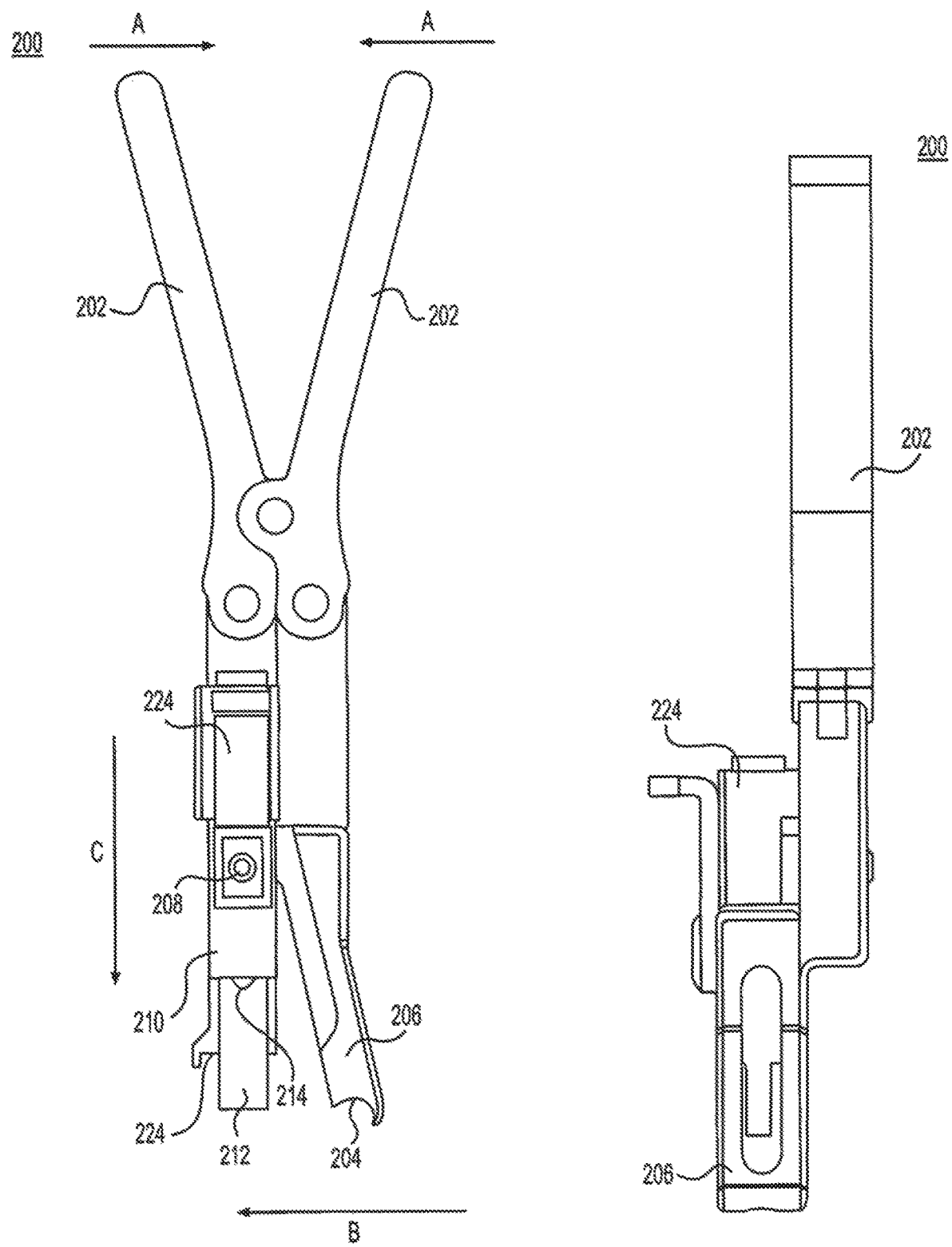
FIG. 13 is a front view of an embodiment of a bi-lateral reducer in accordance with the present invention.
FIG. 14 is a side view of the bi-lateral reducer.
Figure 15:
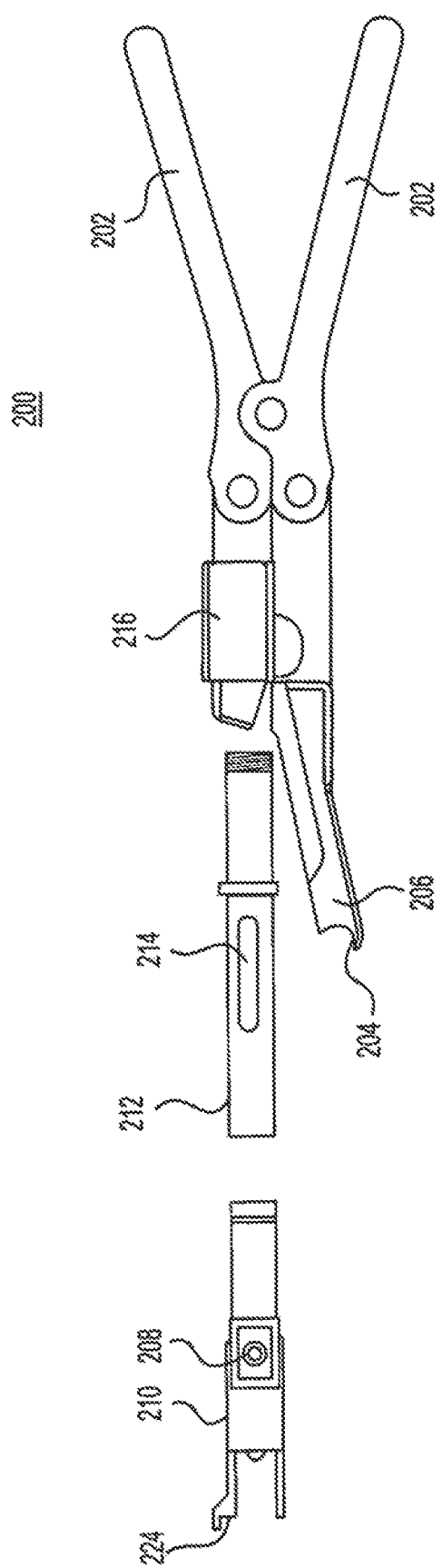
FIG. 15 is an exploded view of the bi-lateral reducer.
Figure 16:
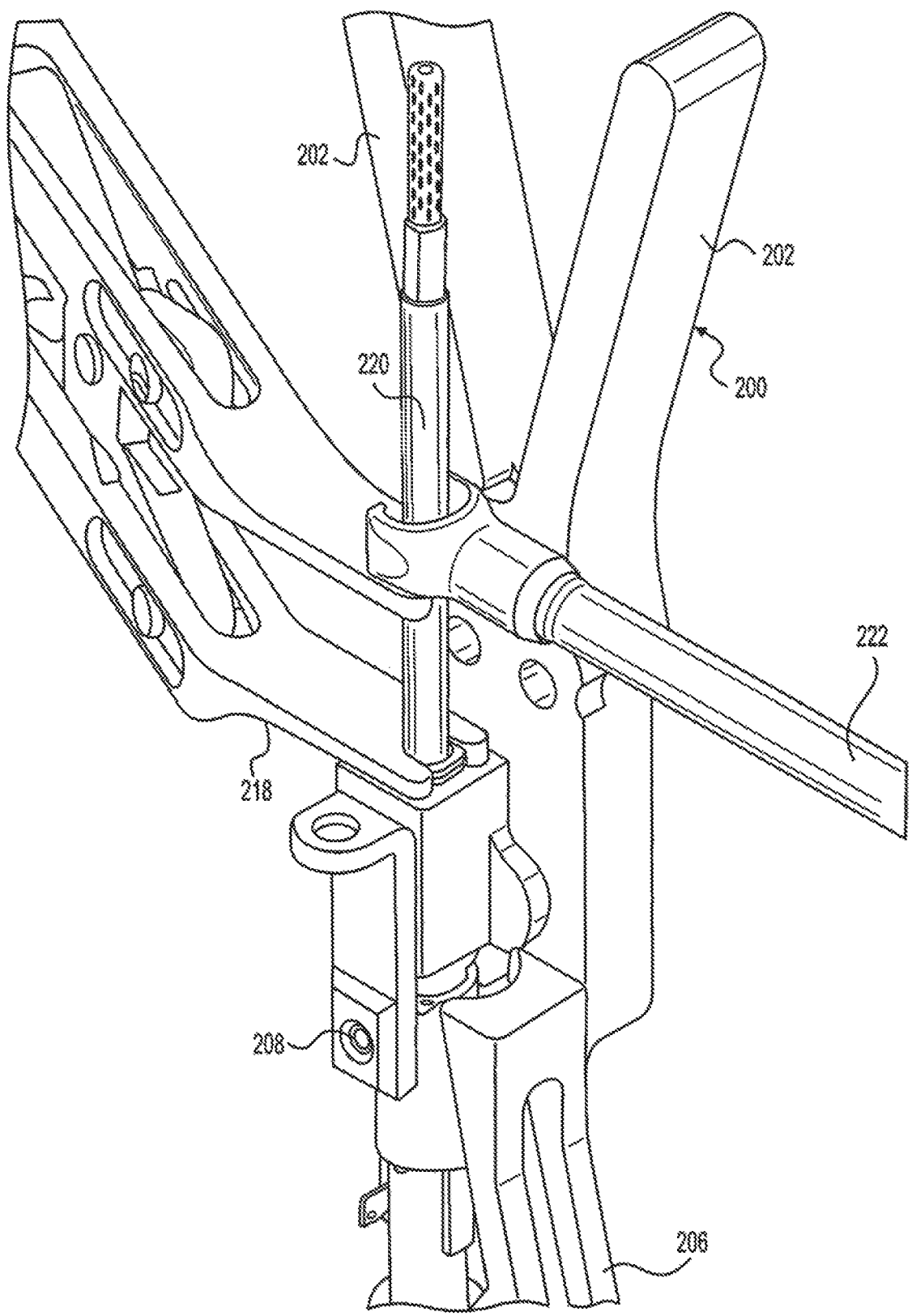
FIG. 16 is a partial perspective view of the bi-lateral reducer with the sagittal reducer and rotation arm attached to the screw stick.
Figure 17:
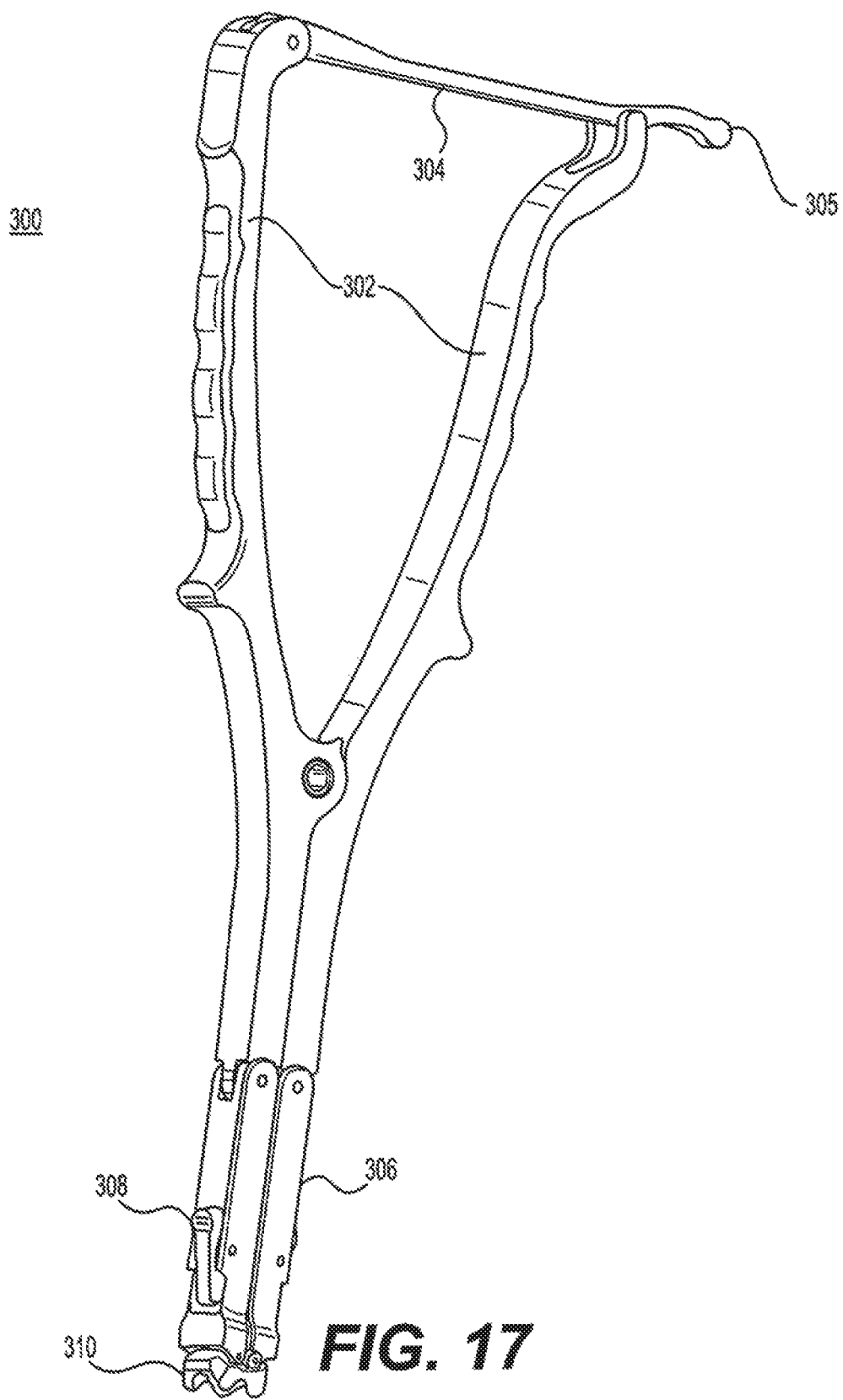
FIG. 17 is a perspective view of an embodiment of hinged tab breaker in accordance with the present invention.

Rotation of the enlarged knobbed wheel rotates the drive shaft, which rotates the connection tip. This provides for attaching or removing the intervertebral spacer inserter from a spacer 131 as illustrated in FIGS. 10-12. Attachment and removal of the intervertebral spacer inserter involves threading the connection tip either into or out of a corresponding threaded shaft 190 or connection hole in the spacer. This threaded shaft is offset from the center line 192 of the spacer. Therefore, the sliding tip 126 is placed in either the first position (FIG. 12) or the second position (FIG. 11) so that the connection tip aligns with the threaded shaft when the spacer is centered between the tabs 141 of the sliding tip. This provides for either a left or right side lateral approach to the spine with the spacer extending the defined angle 194 from the longitudinal axis of the sleeve. This provides access to L4-L5 disc level and the upper levels of the lumbar cord through LLIF using spacers with an off-centered point of connection for both right and left approaches.

Referring to FIGS. 13-16, the present invention is also directed to a bi-lateral reducer 200 that is used to reduce a rod into an implant to achieve coronal plane reduction. In general, a side-loading pedicle screw system requires a tool to reduce the rod into the implant to achieve coronal plane reduction while still allowing sagittal plane reduction to have the screw head meet the rod construction. The bi-lateral reducer of the present invention combines coronal reduction with implant rod holding sleeve insertion in the same tool. Sagittal reduction and implant rotation for alignment are achieved using additional instruments that are attached to the bi-lateral reducer. Therefore, the bi-lateral reducer provides for both coronal plane reduction and sagittal plane reduction with a side-loading pedicle screw and rod implant.

In general, the bi-lateral reducer uses a plurality of structures or armatures connected by a plurality of pins to provide coronal reduction. The bi-lateral reducer includes a pair of handles 202 pivotally attached to each other. To one handle a rod slot arm 206 is pivotally attached. The rod slot arm 206 includes a rod slot 204 on an end opposite the point of attachment of the rod slot arm to the handle. The rod slot end includes a curvature that is suitable for engaging and moving a rod. Pivotally attached to the other handle is a guide shaft attachment point 224. A screw stick guide shaft 212 is inserted into the guide shaft attachment point and secured to the bi-lateral reducer. A tulip sleeve inserter 210 slides over the screw stick guide shaft. The tulip sleeve inserter includes a set screw 208. When the tulip sleeve inserter is placed over the screw stick guide shaft, the set screw is turned to engage in a slot 214 in the screw stick guide shaft. This prevents removal of the tulip sleeve inserter and defines a range of motion of the tulip sleeve inserter along the screw stick guide shaft. An end 224 of the tulip sleeve inserter is configured to secure a rod holding sleeve (not shown) for positioning over the rod following reduction. The additional tools for the bi-lateral reducer include a rotation arm 222 and a sagittal reducer 218.

In order to use the bi-lateral reducer, a rod holding sleeve is attached to the end of the tulip sleeve inserter. The tulip sleeve inserter and the screw stick guide shaft are slid over a screw stick 220 that is attached to a patient implant. The bi-lateral reducer includes a precision stick guide shaft to provide a close fit to the screw stick. The screw stick extends past the guide shaft attachment point, and the rotation arm is attached to this exposed top portion of the screw stick. The sagittal reducer is also attached to the top portion of the screw stick between the rotation arm and the guide shaft attachment point. Moving the handles together in the direction of arrow A, moves the rod slot arm 206 in the direction of arrow B. This engages the rod slot onto the rod, reducing the rod into the side loading pedicle screw implant. Preferably, the handles are ratcheted to assist in reduction and to prevent the rod from moving backwards once reduced, i.e., to hold the handles in the closed position. Following reduction of the rod, the tulip sleeve inserter is moved in the direction of arrow C to insert the rod holding sleeve onto the implant. With the rod reduced and held in place with the sleeve, the bi-lateral reducer is removed, and a locking nut is attached to more permanently secure the rod.

The bi-lateral reducer reduces through the coronal plane, and the additional tools attached to the screw stick provide sagittal reduction and rotation of the implant. Rotation of the implant may be required to align the rod with the rod slot for proper reduction. Sagittal reduction is achieved by applying distractive forces between the bi-lateral reducer and the implant through the screw stick. Therefore, complete reduction of the rod is achieved without removing any of the instruments. The bi-lateral reducer simplifies the surgical procedure and allows complete reduction and alignment of the rod to the implant as well as locking the rod into the implant without removing any tools. By using the screwstick on the implant, the bi-lateral reducer is easily aligned and attached to the implant for rigid, assured reduction.

Referring to FIGS. 17-22, the present invention is also directed to a hinged tab breaker 300 for a reduction screw that can simultaneously remove both tabs from a single reduction screw. Typically, tabs are removed from reduction screws using an instrument that grabs and breaks each individual tab one at a time. Since each reduction screw has two tabs and procedures may use a number of screws, the single tab breaking method is tedious and time consuming. The hinged tab breaker of the present invention breaks and removes both tabs from a single reduction screw simultaneously, reliably and easily.

Figure 21:
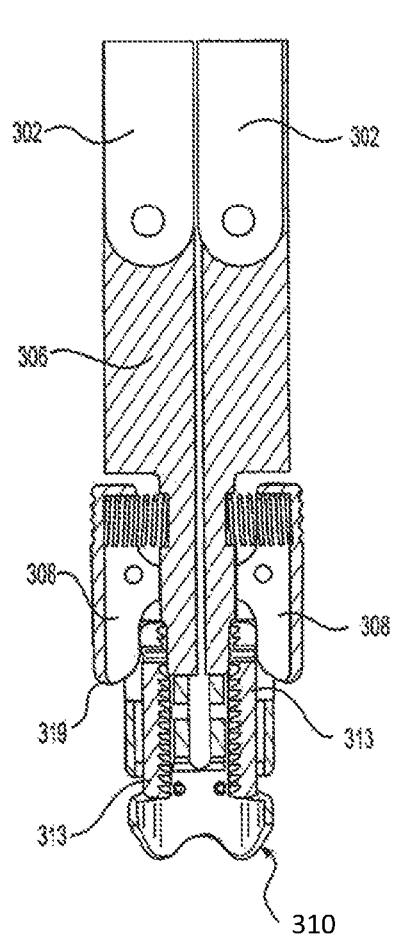
FIG. 21 is a partial cutaway view of an end of the hinged tab breaker with the screws tabs removed form the reducing screw.
Figure 22:
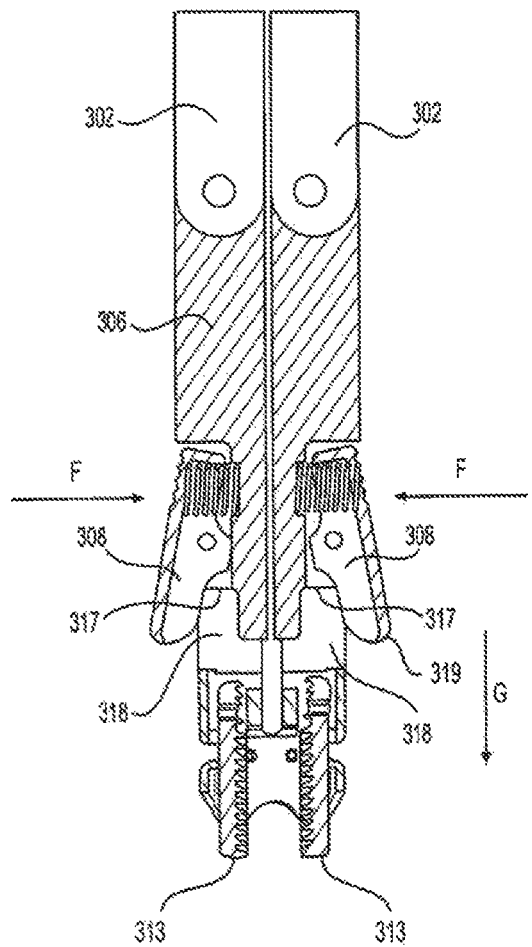
FIG. 22 is a partial cutaway view of an end of the hinged tab breaker with the screws tabs ejected from the hinged tab breaker

As illustrated, the hinged tab breaker 300 includes a pair of handle arms 302 attached at one end by a ratcheting arm 304. Therefore, when the arms are moved toward each other, they are held or locked in the position by the ratcheting arm, which includes a releasing tab 305 to release the arms for opening. A tip 306 is attached to the other end of the each arm. The tip is arranged as two identical tip portions set as mirror images of each other. Each tip portion of the tip includes a press tab 308 that can pivot with respect to the tip between a closed position (FIGS. 20 and 21) and an open position (FIG. 22). This pivotal movement exposes a retaining window 318 inside each tip portion. Each press tab is biased in the closed position by a spring 316 or other suitable biasing member. Pressing of the tabs in the direction of arrows F, moves the tabs to the open position. A tulip collar 310 is attached to the end of the tip. The tulip collar is shaped to fit around the tulip head of the reduction screw and to cradle the rod 303 that is passing through the reduction screw.

Figure 18:
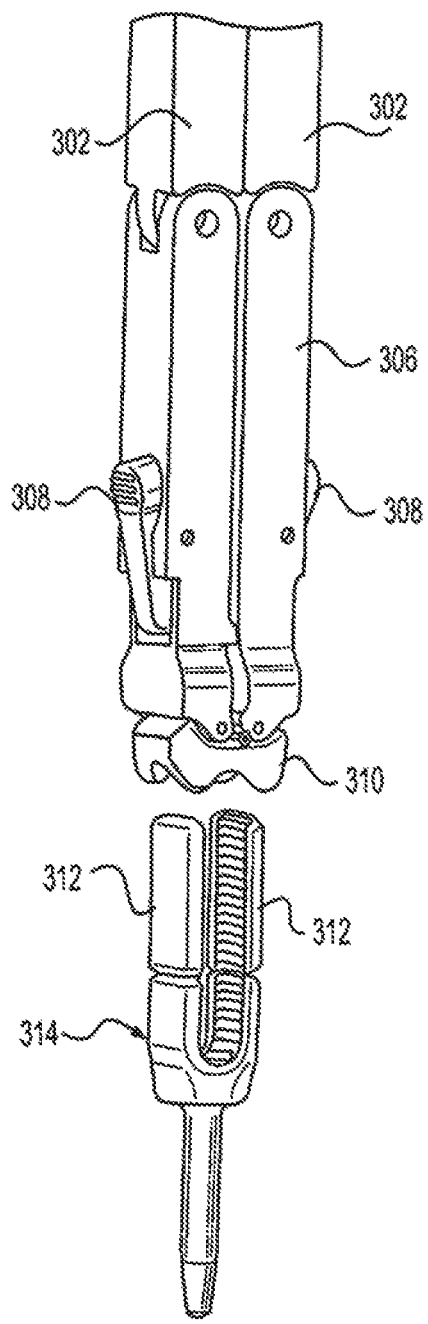
FIG. 18 is a partial perspective view of an end of the hinged tab breaker positioned over a reducing screw.
Figure 19:
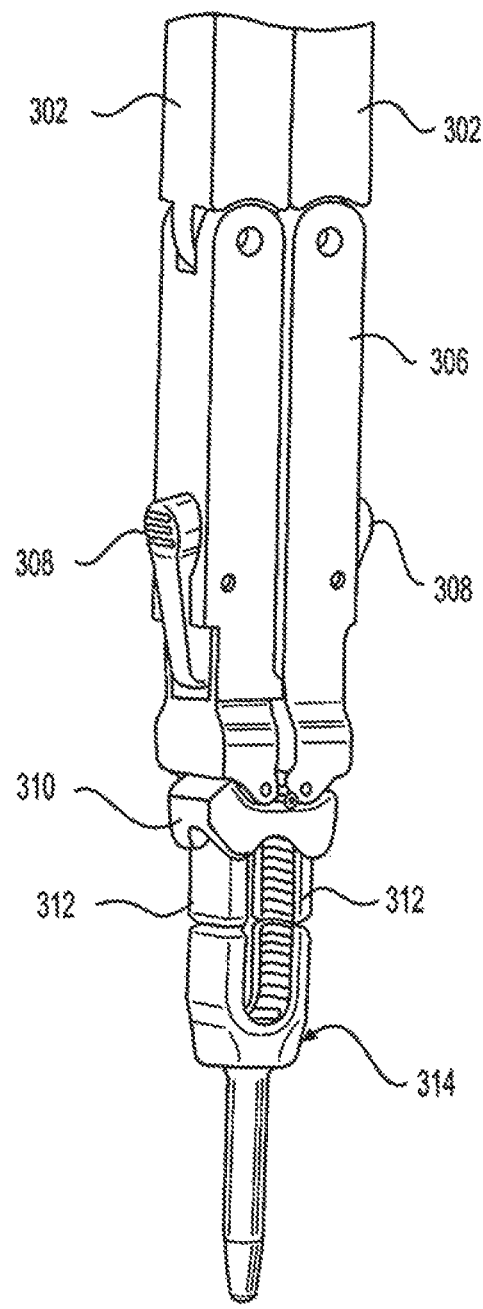
FIG. 19 is a partial perspective view of an end of the hinged tab breaker positioned over a reducing screw with the screws tabs inserted into the hinged tab breaker.
Figure 20:
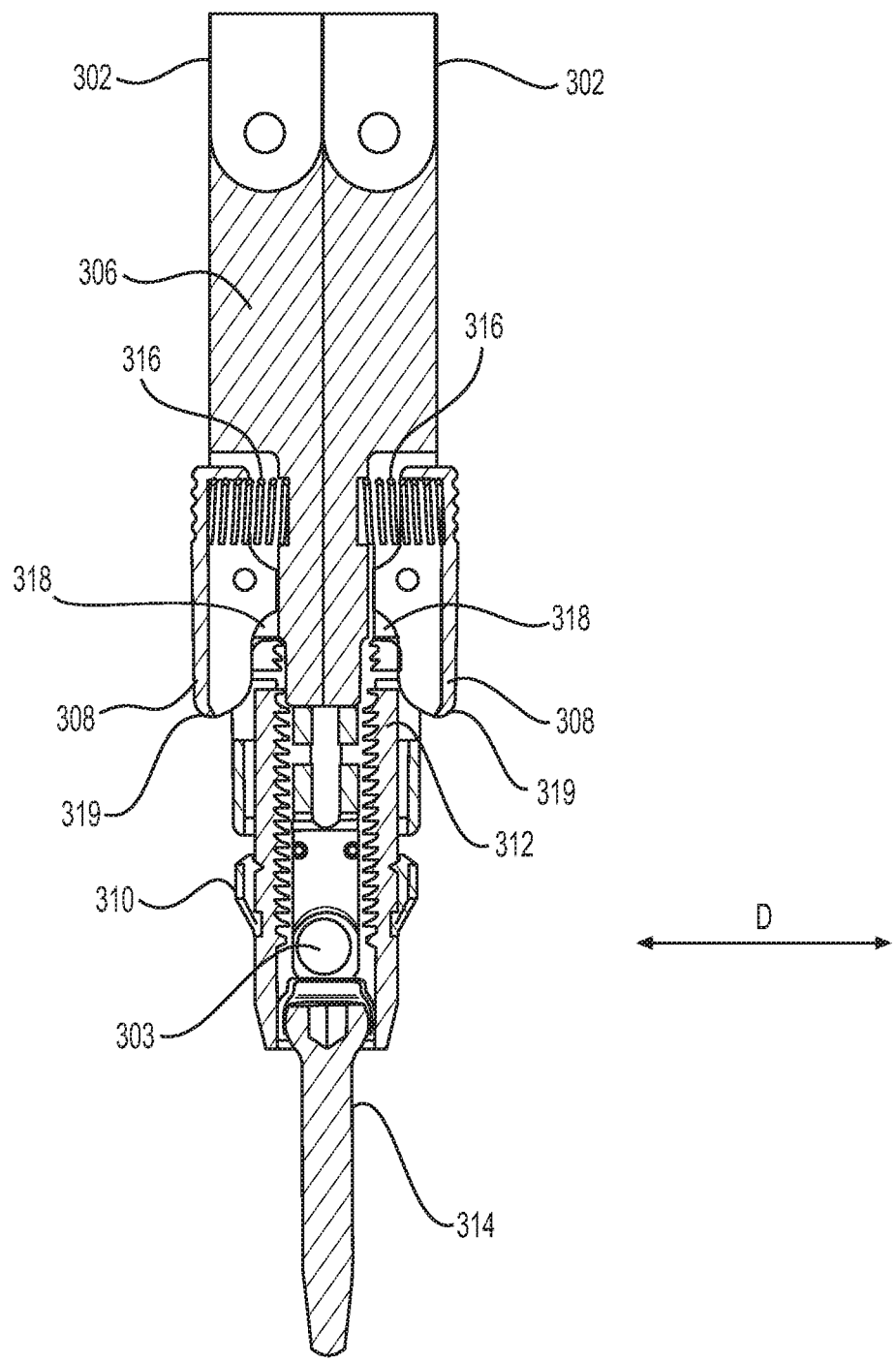
FIG. 20 is a partial cutaway view of an end of the hinged tab breaker positioned over a reducing screw with the screws tabs inserted into the hinged tab breaker

The hinged tab breaker 300 is placed over the reduction screw 314 with the tulip collar located over tulip head and the tabs 312 of the reduction screw (FIG. 18). The tulip collar is slid down over the tabs (FIG. 19), allowing the reduction screw tabs 312 to pass under the spring-loaded press tabs and into the retaining windows (FIG. 20). The leading edge 319 of each press tab can be rounded, beveled, sloped or chamfered to facilitate passage of the screw tabs into the retaining windows 318. The hinged tab breaker is lowered around the reduction screw until the screw tabs are seated against the back walls 317 of the retaining windows 318 in the tip of the hinged tab breaker. The handles are then squeezed together. The hinged handle arrangement bends the tabs of the reduction screw outward simultaneously, and pressure is applied on the reduction screw tabs by rocking the hinged tab breaker back and forth in the direction of arrow D until the screw tabs break away from the tulip head of the reduction screw. At this point, the hinged tab breaker is moved away from the reduction screw with the reduction screw tabs retained within the tip (FIG. 21). Therefore, the broken reduction screw tabs 313 can be removed from the area of the reduction screws. Pressing the tabs 308 in the direction of arrows F releases the broken reduction screw tabs 313 which pass out of the hinged tab breaker through the tulip collar in the direction of arrow G (FIG. 22).

By fitting around and stabilizing the lower part of the tulip head, the hinged tab breaker remains centered about the implant and equally distributes the breaking force across both tabs. The tabs of the reduction screw fit into pockets or retaining windows 318 in the tips of the instrument, which are controlled to ensure that the instrument breaks the tabs at the desired location along the length of each screw tab. Spring-loaded press tabs pinch against the tabs and retain them within the tips of the instrument. These components are rounded on the leading edge to allow the tabs of the reduction screw to slide under them with little resistance upon insertion. The press tabs retain the tabs of the reduction screw after they are broken away from the implant to facilitate easy removal. Compression of the spring under the press tabs allows easy release of the broken tabs for disposal.

Referring to FIGS. 23-25, the present invention is also directed to a retractable rigid screwdriver 400 for the insertion of pedicle screws or other bony anchors. The retractable rigid screw driver includes a retracting mechanism that prevents the screwdriver from becoming loose during anchor insertion and allows for the retraction of the screw holding mechanism in-situ to provide visibility for driving the screw. The retractable rigid screwdriver 400 includes a handle 402 that is threaded onto a tightening shaft 404. The handle can be removed, i.e., unscrewed, from the tightening shaft, and the tightening shaft and handle, when attached, can rotate independent of each other. The retractable rigid screwdriver also includes a retracting shaft 418 that can fit inside the tightening shaft. The retracting shaft includes one or more splayed tabs 422 that engage windows 406 running along the side of the tightening shaft. Engagement of the splayed tabs in the windows holds the tightening shaft 404 over the retracting shaft 416. This also provides alignment between a gripping end 424 of the retracting shaft and a compression collar end 408 of the tightening shaft. Removing the handle and depressing the splayed tabs permits complete removal of tightening shaft from the retractable rigid screwdriver for cleaning. The gripping end is split into a plurality of tabs or fingers, and when the compression collar end is over the gripping end, the fingers are compressed and hold a screw for insertion and alignment. When the splayed tabs are depressed, the tightening shaft is moved in the direction of arrow H to uncover the gripping end.

A driver shaft 410 passes completely through the handle, tightening shaft and retracting shaft. The driver shaft includes a proximal end 412 extending past the handle and shaped to engage a driving device such as a wrench or other suitable driver. Suitable shapes for this proximal end include, but are not limited to square and hex heads. The distal end 414 of the driver shaft opposite the proximal end is shaped to engage a screw or bony anchor to rotate the anchor and drive the anchor into the desired location in a bone. The distal end is generally disposed adjacent the gripping end 424 of the retracting shaft. A transverse pin 416 is provided in the driver shaft. This pin engages an elongated slot 420 on the retracting shaft to define the range of motion of the retracting shaft relative to the driver shaft. One end of this elongated slot includes a spring lock 419 to hold the retracting shaft in a retractable position that exposes the distal end of the driver shaft.

A screw is placed in the gripping end of the retracting shaft. This screw also engages the distal end of the driving shaft. The screw is moved into alignment with the desired location for insertion. The retracting shaft and tightening shaft are then moved in the direction of arrow H to disengage the screw from the gripping end and to expose the screw. The retracting shaft and tightening shaft are moved until the transverse pin engages the spring lock in the elongated slot to hold the retractable rigid screwdriver in the retracted position. The screw is still engaged with the distal end of the driving shaft. This provides increased visibility of the screw during rotation and driving of the screw by the driving shaft.

While it is apparent that the illustrative embodiments of the invention disclosed herein fulfill the objectives of the present invention, it is appreciated that numerous modifications and other embodiments may be devised by those skilled in the art. Additionally, feature(s) and/or element(s) from any embodiment may be used singly or in combination with other embodiment(s) and steps or elements from methods in accordance with the present invention can be executed or performed in any suitable order. Therefore, it will be understood that the appended claims are intended to cover all such modifications and embodiments, which would come within the spirit and scope of the present invention.

What is claimed is:

1. A tab breaker instrument comprising:
   a body portion having a pair of handle arms at a first end;
   a tip portion attached to the body portion at a second end, wherein the tip portion is arranged as two identical portions, each portion capable of receiving a reduction pedicle screw, wherein the reduction pedicle screw includes a tulip head and a pair of reduction tabs disposed on the tulip head; and
   a collar portion attached to the tip portion, the collar portion being configured and dimensioned to fit around the pair of reduction tabs and the tulip portion of the reduction pedicle screw,
   wherein the body portion is configured to bend the pair of reduction tabs outwardly when a force is applied to the pair of handles to simultaneously break the pair of reduction tabs off of the tulip head of the reduction pedicle screw, and
   wherein the reduction tabs are retained in the body portion by biased press tabs after being broken off from the tulip head of the reduction pedicle screw.

2. The instrument of claim 1, wherein each tip portion includes a press tab of the biased press tabs.

3. The instrument of claim 2, wherein the press tab is capable of moving each tip portion from an open position to a closed position.

4. The instrument of claim 3, wherein each tip portion is biased to the closed position by a biasing member.

5. The instrument of claim 3, wherein a leading edge of the press tab is shaped to facilitate passage of the reduction tabs of the pedicle screw.

6. The instrument of claim 1, further comprising a locking arm, wherein the locking arm engages at least one of the two handle arms to lock the handle arms in a desired position.

7. The instrument of claim 6, wherein the locking arm includes a releasing tab to disengage the locking arm from at least one of the two handle arms.

8. The instrument of claim 7, wherein the locking arm is a ratchet arm to lock the handle arms in a desired position.

9. The instrument of claim 1, wherein the two identical portions of the tip portion are mirror images of each other.

10. The instrument of claim 1, wherein the instrument breaks each reduction tab of the reduction pedicle screw without having to disengage the instrument from the reduction pedicle screw.

* * * * *